United States Patent
Benser

(10) Patent No.: US 7,706,881 B1
(45) Date of Patent: Apr. 27, 2010

(54) IMPLANTABLE MEDICAL DEVICE WITH CARDIAC OUTPUT- BASED APNEA SUPPRESSION

(75) Inventor: Michael Benser, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 1017 days.

(21) Appl. No.: 11/417,959

(22) Filed: May 3, 2006

(51) Int. Cl.
A61N 1/365 (2006.01)
(52) U.S. Cl. .................................. 607/24
(58) Field of Classification Search .......... 607/9, 607/17–18, 19, 20, 23–24; 600/508–510, 600/513, 526
See application file for complete search history.

(56) References Cited

U.S. PATENT DOCUMENTS

| | | | |
|---|---|---|---|
| 5,476,483 A | 12/1995 | Bornzin et al. | 607/17 |
| 6,128,534 A | 10/2000 | Park et al. | 607/17 |
| 6,622,045 B2 | 9/2003 | Snell et al. | 607/30 |
| 6,881,192 B1 | 4/2005 | Park | 600/529 |
| 6,904,320 B2 | 6/2005 | Park et al. | 607/17 |
| 2004/0138718 A1* | 7/2004 | Limousin et al. | 607/17 |
| 2004/0186523 A1 | 9/2004 | Florio | 607/17 |
| 2005/0090871 A1 | 4/2005 | Cho et al. | 607/17 |
| 2005/0240240 A1 | 10/2005 | Park et al. | 607/42 |
| 2005/0288728 A1 | 12/2005 | Libbus et al. | 607/42 |
| 2005/0288729 A1 | 12/2005 | Libbus et al. | 607/42 |

FOREIGN PATENT DOCUMENTS

EP    1 459 785 A1    9/2004

OTHER PUBLICATIONS

Stephane Garrigue, M.D. et al., "Benefit of Atrial Pacing in Sleep Apnea Syndrome", N. Engl J Med, Feb. 2002; vol. 346, No. 6, pp. 404-412.

* cited by examiner

Primary Examiner—Kennedy J. Schaetzle
Assistant Examiner—Jessica Sarcione

(57) ABSTRACT

Techniques are provided for improving cardiac output and also suppressing certain forms of apnea/hypopnea within a patient using an implantable medical device, such as a pacemaker or ICD. In one example, a selected pacing parameter—usually the pacing rate—is temporarily altered by an amount sufficient to elevate cardiac output, the elevation in cardiac output being eventually reduced by intrinsic compensatory mechanisms within the patient. The pacing parameter is then temporarily reset for a duration sufficient to allow the compensatory mechanisms to return toward a previous state so as to permit a subsequent alteration in the pacing parameter to again elevate cardiac output. The pacing parameter is repeatedly altered and reset so as to achieve an overall increase in cardiac output despite the intrinsic compensatory mechanisms. The increase in cardiac output is often sufficient to suppress certain forms of apnea/hypopnea, particularly apnea/hypopnea arising from Cheyne-Stokes Respiration (CSR).

20 Claims, 10 Drawing Sheets

IMPLANTABLE MEDICAL DEVICE WITH CARDIAC OUTPUT-BASED APNEA SUPPRESSION

FIELD OF THE INVENTION

The invention generally relates to implantable medical devices, such as pacemakers or implantable cardioverter/defibrillators (ICDs), and in particular to techniques for enhancing cardiac output and suppressing apnea and/or hypopnea within a patient in which a medical device is implanted.

BACKGROUND OF THE INVENTION

Apnea and hypopnea are forms of disordered breathing characterized by periods of significantly reduced respiration. With hypopnea, respiration is reduced but still present. With apnea, however, respiration may cease completely for a minute or longer. Apnea most commonly occurs while the patient is asleep. Indeed, individual episodes of sleep apnea can occur hundreds of times during a single night. Accordingly, patients with apnea often experience excessive fatigue during the day. In addition, apnea can exacerbate various medical conditions, particularly congestive heart failure (CHF) wherein the patient suffers from poor cardiac function. Other medical conditions that can be adversely affected by apnea include: high blood pressure, risk for heart attack and stroke, memory problems, impotency and sexual dysfunction, migraine headaches, depression and anxiety, polycythemia (increase in the number of red blood cells), cor pulmonale (an alteration in the structure and function of the right ventricle caused by a primary disorder of the respiratory system), bradycardia (excessively slow heart rate), tachycardia (excessively fast heart rate), pulmonary hypertension hypoxemia (chronic daytime low blood oxygen) and hypercapnia (increased blood carbon dioxide ($CO_2$)).

Apnea is often associated with Cheyne-Stokes Respiration (CSR), which is an abnormal respiratory pattern occurring in some patients with congestive heart failure (CHF). CSR is characterized by alternating periods of hypopnea and hyperpnea (i.e. fast, deep breathing.) Briefly, respiration is regulated by groups of nerve cells in the brain in response to changing blood chemistry levels, particularly blood $CO_2$ levels. When blood $CO_2$ levels exceed a certain threshold, the groups of nerve cells generate a burst of nerve signals for triggering inspiration. The inspiration nerve signals are relayed via phrenic nerves to the diaphragm and via other nerves to chest wall muscles, which collectively contract to expand the lungs. CSR arises partly due to a time lag between blood $CO_2$ levels sensed by the respiratory control nerve centers of the brain and the blood $CO_2$ levels. With CHF, poor cardiac function results in poor blood flow to the brain such that the nerve centers respond to blood $CO_2$ levels that are no longer properly representative of the overall blood $CO_2$ levels in the body. Hence, the nerve centers trigger an increase in the depth and frequency of breathing in an attempt to compensate for perceived high blood $CO_2$ levels—although the blood $CO_2$ levels will have already dropped. By the time the respiratory control nerve centers detect the drop in blood $CO_2$ levels and act to slow respiration, the blood $CO_2$ levels will have already increased. This cycle becomes increasingly unbalanced until respiration alternates between hypopnea and hyperpnea. The periods of hypopnea often become sufficiently severe that no breathing occurs between the periods of hyperpnea, i.e. periods of frank apnea occur between the periods of hyperpnea. The fluctuating blood chemistry levels caused by alternating between hyperpnea and apnea/hypopnea can significantly exacerbate CHF and other medical conditions. When CHF is still mild, CSR occurs, if at all, only while the patient is sleeping. When it becomes more severe, CSR can occur while the patient is awake. Accordingly, CSR is one mechanism by which apnea can occur while a patient is awake. Hence, apnea is not limited to occurring only while a patient is asleep.

Herein, apnea arising due to CSR is referred to as "CSR-induced apnea." Hypopnea arising due to CSR is referred to as "CSR-induced hypopnea." For the sake of generality, the term "CSR-induced apnea/hypopnea" is used to encompass both conditions. Note that, in some of the medical literature, apnea arising due to CSR is referred to as "CSA-CSR," where CSA stands for "Central Sleep Apnea." However, as noted, CSR-induced apnea can potentially occur while the patient is awake and hence is not necessarily a form of sleep apnea. Moreover, the term CSA also refers to a fundamentally different type of apnea, which is believed to be the result of a neurological condition within the central nervous system. With CSA, phrenic nerve signals are simply not generated during extended periods of time while the patient is asleep or are of insufficient magnitude to trigger sufficient muscle contraction to achieve inhalation. This occurs regardless of the blood $CO_2$ levels and hence appears to be unrelated to CSR-induced forms of apnea. Herein, to avoid any possible confusion, the term CSR-CSA is not used. As noted, the term CSR-induced apnea/hypopnea is instead used. Note, also, that there is yet another form of apnea—obstructive sleep apnea (OSA). OSA arises when the respiration airway is temporarily blocked. OSA is not particularly relevant to the techniques described herein but is mentioned for the sake of completeness.

In view of the adverse consequences of CSR-induced apnea/hypopnea, it is highly desirable to provide techniques for suppressing episodes of the condition. A variety of techniques have been proposed, particularly for use by pacemakers, ICDs or other implantable medical devices. With many such techniques, the implantable device first detects an episode of apnea/hypopnea and then delivers therapy to alleviate the episode. Examples of techniques for detecting episodes of apnea/hypopnea are discussed in U.S. patent application Ser. No. 10/883,857, of Koh et al., entitled "System and Method for Real-Time Apnea/Hypopnea Detection Using an Implantable Medical System," filed Jun. 30, 2004. See, also, U.S. patent application Ser. No. 10/795,009, of Koh, entitled "System and Method for Distinguishing among Obstructive Sleep Apnea, Central Sleep Apnea and Normal Sleep Using an Implantable Medical System," filed Mar. 4, 2004 and U.S. patent application Ser. No. 10/844,023, of Koh, filed May 11, 2004, entitled "System and Method for Providing Demand-Based Cheyne-Stokes Respiration Therapy Using an Implantable Medical Device". Once an episode of apnea/hypopnea is detected, therapy is delivered to terminate the episode and restore respiration that is more normal. Exemplary techniques include applying electrical stimulation directly to the phrenic nerves via implantable nerve stimulators so as to cause the diaphragm to contract. These and other therapeutic techniques are discussed in the aforementioned patent applications as well. If therapy is ineffective, warning signals can be generated to awaken the patient, which is typically sufficient to restore normal respiration.

It would be preferable, however, to provide techniques for suppressing CSR-induced apnea/hypopnea that do not require detecting individual episodes of apnea or hypopnea, as reliable detection can sometimes be problematic. It would also be desirable to provide suppression therapies that do not require phrenic nerve stimulators or other potentially elaborate or intrusive therapeutic measures. One technique that has been proposed is simply to increase a cardiac pacing rate so as to increase cardiac output. So long as the stroke volume of the heart remains constant, an increase in the cardiac pacing rate produces an increase in cardiac output. The increase in cardiac output tends to suppress CSR by increasing the blood flow to the brain thus avoiding the blood $CO_2$ imbalances described above. Suppression of CSR, in turn, suppresses CSR-induced episodes of apnea/hypopnea. However, it is believed by the inventor of the present invention that the increase in cardiac output resulting from an increase in pacing rate is only temporary. This is illustrated in FIG. 1. Briefly, a cardiac pacing rate 2 is increased at time 3 resulting in an increase in cardiac output 4. The increase in cardiac output suppresses CSR, which is illustrated in the figure by way of a respiratory pattern 5 having crescendo/decrescendo patterns alternating between hyperpnea 5 and apnea 6. The increase in cardiac output is sufficient to temporarily diminish the severity of CSR thus permitting more normal respiration 7 to resume. However, as illustrated in the figure, the increase in cardiac output does not last, even though the higher pacing rate is sustained for an extended period of time. The cardiac output soon begins to drop, apparently due to intrinsic hemodynamic compensatory mechanisms within the patient. In this regard, hemodynamic systems of the patient appear to operate to reduce the stroke volume to compensate for the artificially increased heart rate. As a result, CSR eventually resumes (or it again becomes more severe), thus triggering further episodes of apnea. Note that the graphs of FIG. 1 should not be construed as depicting actual clinically-obtained data. The graphs set forth hypothetical data provided to clearly illustrate the affect of the intrinsic compensatory mechanisms on cardiac output and respiration. Actual variations in cardiac output and respiration may differ. Also note that, during actual CSR, the intervals of apnea/hypopnea are often longer in duration than the intervening intervals of hyperpnea. FIG. 1 illustrates relatively short intervals of apnea/hypopnea so as to permit many complete cycles of CSR to be illustrated within the timeline of the figure. The vertical scales of the graphs are in arbitrary units and the features illustrated therein are not necessarily to scale.

It would be highly desirable to provide techniques for use by an implantable medical device for achieving a sustained increase in cardiac output sufficient to suppress apnea/hypopnea, particularly CSR-induced apnea/hypopnea. It is to this end that certain aspects of the invention are directed. Although a sustained increase in cardiac output is helpful in suppressing apnea/hypopnea, the increase is beneficial in and of itself, since increased cardiac output tends to mitigate CHF, pulmonary edema, and other conditions. Accordingly, other aspects of the invention are directed to the more general goal of improving cardiac output within a patient using an implantable medical device.

SUMMARY

In accordance with one illustrative embodiment, techniques are provided for improving cardiac output within a patient using an implantable medical device, such as a pacemaker or ICD. In one embodiment, a selected pacing parameter—usually the pacing rate—is temporarily altered by an amount sufficient to elevate cardiac output, the elevation in cardiac output being eventually reduced by intrinsic compensatory mechanisms within the patient. The pacing parameter is then temporarily reset for a duration sufficient to allow the compensatory mechanisms to return toward a previous state so as to permit a subsequent alteration in the pacing parameter to again elevate cardiac output. The pacing parameter is repeatedly altered and reset so as to achieve an overall increase in cardiac output despite the intrinsic compensatory mechanisms.

In one implementation, the pacing parameter that is repeatedly altered and reset is the cardiac pacing rate. Briefly, the pacing rate is increased to achieve a temporary increase in cardiac output. Once the intrinsic compensatory mechanisms within the patient begin to reduce cardiac output, the pacing rate is then reset back to a base pacing rate to allow the compensatory mechanisms to return toward a previous state, thereby permitting a subsequent increase in the pacing rate to again elevate cardiac output. In one specific example, the pacing rate alternates between a base pacing rate ($PR_{BASE}$) and a higher pacing rate ($PR_{HIGH}$) set, e.g., 15 beats per minute (bpm) above the base rate. In one particular implementation, the pacing rate is switched from one rate to another abruptly. In other implementations, the change in pacing rate is performed gradually. In one specific example, the device paces at each rate for five minutes before switching to the other rate. In other examples, a greater percentage of time is spent at the higher pacing rate. For example, the device may pace at $PR_{HIGH}$ for five minutes at a time, then pace at $PR_{BASE}$ for only one minute at a time. Preferably, the pacing rates, the intervals of time spent pacing at the different rates, and the rate of change from one rate to another are all optimized for the particular patient to maximize the average cardiac output. By maximizing average cardiac output, particularly within CHF patients subject to CSR, episodes of CSR can be suppressed, thus suppressing any CSR-induced apnea/hypopnea. In other implementations, the pacing parameter that is repeatedly altered and reset is the AV/PV delay, i.e. the delay between a paced/sensed beat in the atria and delivery of a pacing pulse to the ventricles. In still yet other implementations, the pacing parameter repeatedly altered and reset is the pacing mode, which specifies, at least, which chambers are paced. Exemplary pacing modes include DDI, wherein pacing is performed in both the atria and the ventricles, and VVI, wherein pacing is only performed in the ventricles.

Other aspects of the invention are specifically directed to suppressing CSR-induced apnea/hypopnea. In one such implementation, a selected pacing parameter—again usually the pacing rate—is temporarily altered by an amount sufficient to elevate minimum respiration levels and thereby suppress CSR-induced apnea/hypopnea. The elevation in minimum respiration levels is eventually reduced by intrinsic compensatory mechanisms within the patient. The pacing parameter is then temporarily reset for a duration sufficient to allow the compensatory mechanisms to return toward a previous state so as to permit a subsequent alteration in the pacing parameter to again elevate minimum respiration levels. The pacing parameter is repeatedly altered and reset so as to achieve continued suppression of CSR-induced apnea/hypopnea despite the intrinsic compensatory mechanisms. Typically, the CSR-induced apnea/hypopnea suppression technique is performed only while the patient is asleep, and is hence more prone to CSR-induced apnea/hypopnea. In one specific embodiment, the technique is performed throughout an entire sleep period so as to continuously suppress CSR-induced apnea/hypopnea. This has the advantage of eliminating the need to detect individual episodes of apnea/hypopnea. However, if the implantable medical system has a reliable apnea/hypopnea detector, the technique may instead be demand-based, i.e. otherwise conventional pacing is performed until a first episode of apnea/hypopnea is detected within a given sleep period. Then, the technique is activated to suppress further episodes of apnea/hypopnea within the sleep period. If any individual episodes of apnea persist despite the alternating pacing techniques of the invention, diagnostic data may be transmitted to a bedside monitor for forwarding to a physician or other medical professional for review, or stored within the medical device itself for future review.

BRIEF DESCRIPTION OF THE DRAWINGS

The above and further features, advantages and benefits of the invention will be apparent upon consideration of the descriptions herein taken in conjunction with the accompanying drawings, in which.

DETAILED DESCRIPTION OF THE PREFERRED EMBODIMENTS

The following description includes the best mode presently contemplated for practicing the invention. This description is not to be taken in a limiting sense but is made merely to describe general principles of the invention. The scope of the invention should be ascertained with reference to the issued claims. In the description of the invention that follows, like numerals or reference designators are used to refer to like parts or elements throughout.

Overview of Implantable Medical System

Figure 2:
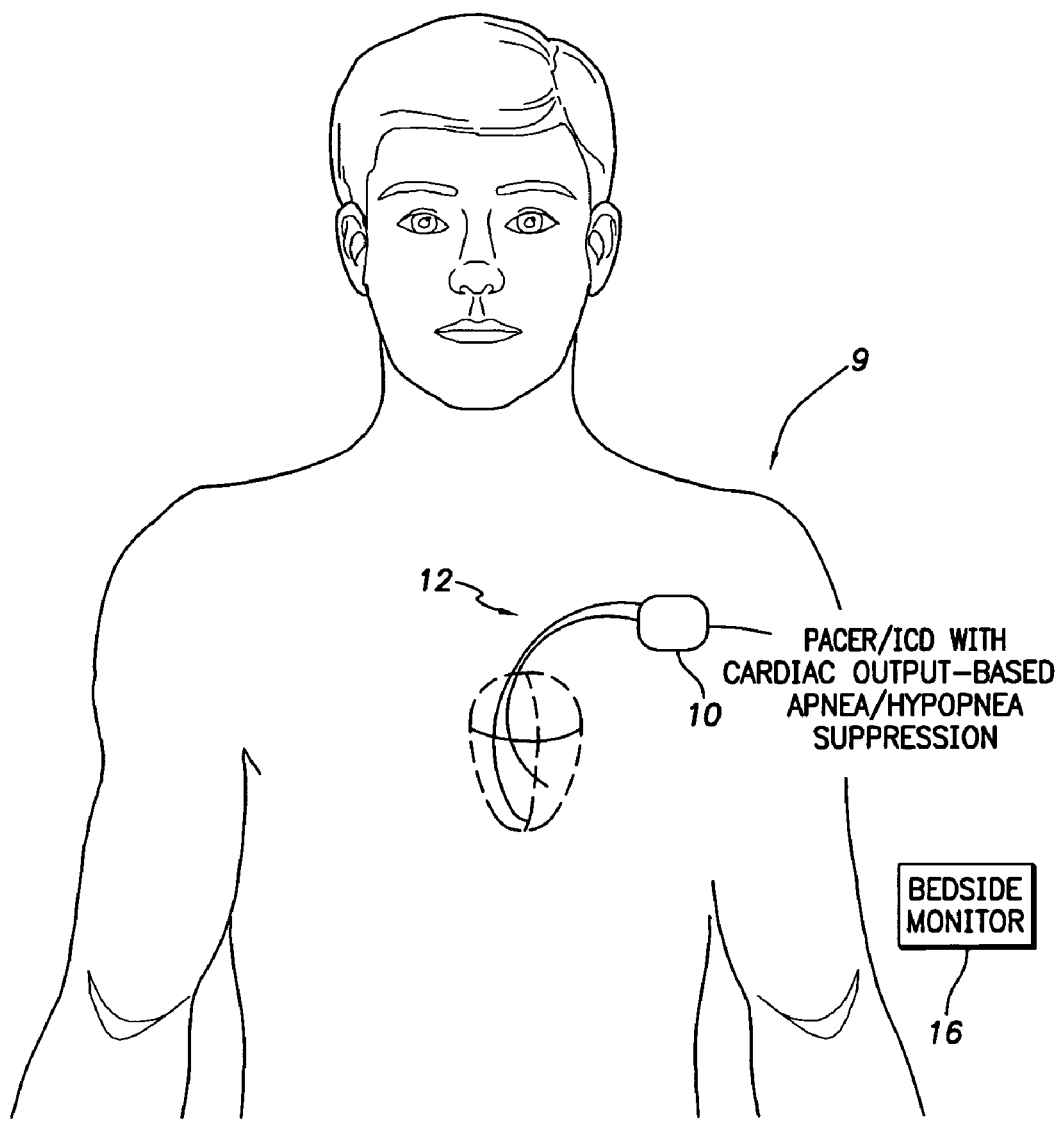
FIG. 2 illustrates pertinent components of an implantable medical system having a pacer/ICD with a cardiac output-based apnea/hypopnea suppression system operative to elevate cardiac output and suppress CSR-induced apnea/hypopnea despite the intrinsic compensatory mechanisms.
Figure 9:
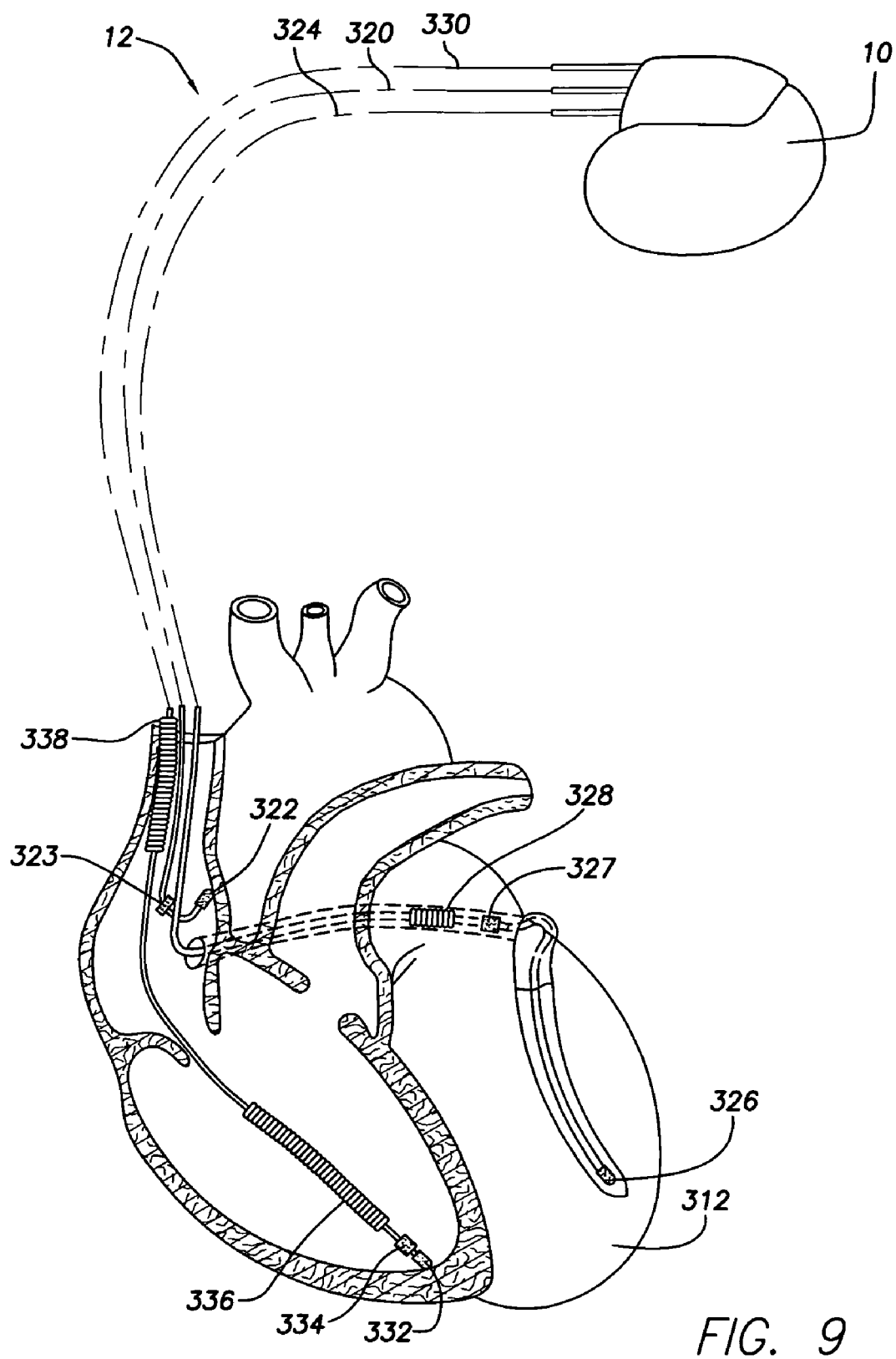
FIG. 9 is a simplified, partly cutaway view, illustrating the pacer/ICD of FIG. 2 along with a more complete set of leads implanted in the heart of a patient.

FIG. 2 illustrates an implantable medical system 9 having a pacer/ICD 10 (or other cardiac stimulation device) equipped with a cardiac output-based apnea/hypopnea suppression system. Briefly, the pacer/ICD repeatedly alters and resets selected pacing parameters—such as pacing rate—so as to elevate cardiac output by an amount sufficient to suppress apnea/hypopnea, particularly apnea/hypopnea arising due to CSR. The elevated cardiac output is achieved despite intrinsic compensatory mechanisms within the patient that might otherwise work to reduce cardiac output following changes in pacing parameters. Pacing therapy is delivered to the heart of the patient in accordance with the selected pacing parameters via a set of cardiac pacing/sensing leads 12, two of which are shown in FIG. 2. A more complete set of exemplary pacing leads are shown in FIG. 9.

Diagnostic data may be transmitted to a bedside monitor 16, which may be networked with other external systems so as to automatically forward diagnostic data to a physician or other medical professional. Alternatively, these diagnostic data may be stored within the medical device itself for future review. A system incorporating bedside monitoring units connected to a centralized external programmer system is described in U.S. Pat. No. 6,622,045 to Snell et al., "System and Method for Remote Programming of Implantable Cardiac Stimulation Devices." For example, if cardiac output has diminished within the patient due to progression of CHF to the point that the suppression techniques of the invention are not capable of preventing frequent episodes of frank apnea, the physician can be notified to take corrective action. Also, if the diagnostic data is representative of an increase in the severity of CSR over time, this may be communicated and/or used as part of an automatic technique to predict the onset time of an acute exacerbation of heart failure.

Thus, FIG. 2 provides an overview of an implantable medical system for elevating cardiac output and suppressing apnea/hypopnea, particularly CSR-induced apnea/hypopnea. The bedside monitor is, of course, also optional. In other implementations, additional components may be provided, such as an implantable warning device or a drug pump for delivering medication in response to CHF or other conditions. These are just a few exemplary embodiments. No attempt is made herein to describe all possible combinations of components that may be provided in accordance with the general principles of the invention.

Figure 3:
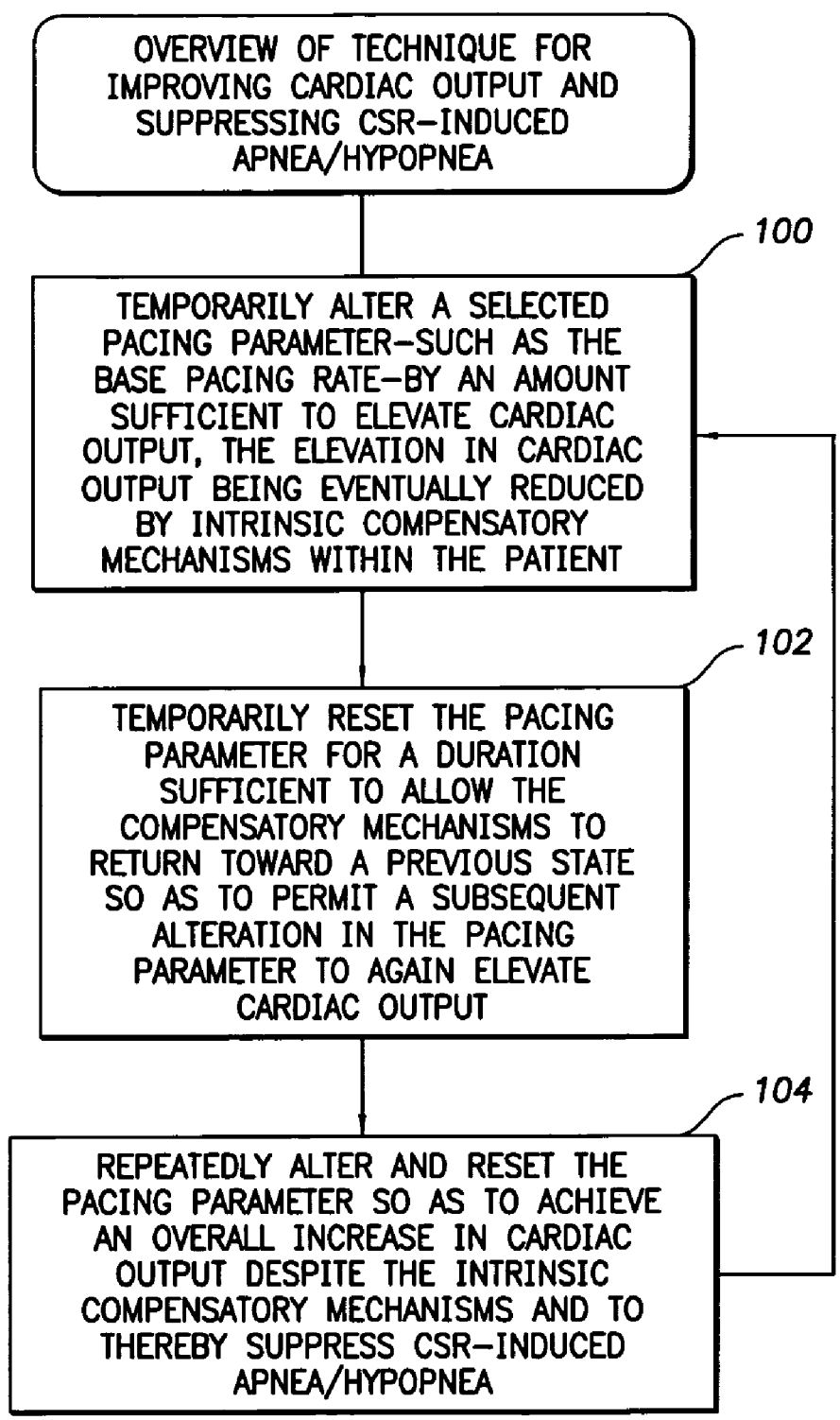
FIG. 3 is a flow diagram providing an overview of the technique for elevating cardiac output and suppressing CSR-induced apnea/hypopnea, which may be performed by the system of FIG. 1.
Figure 4:
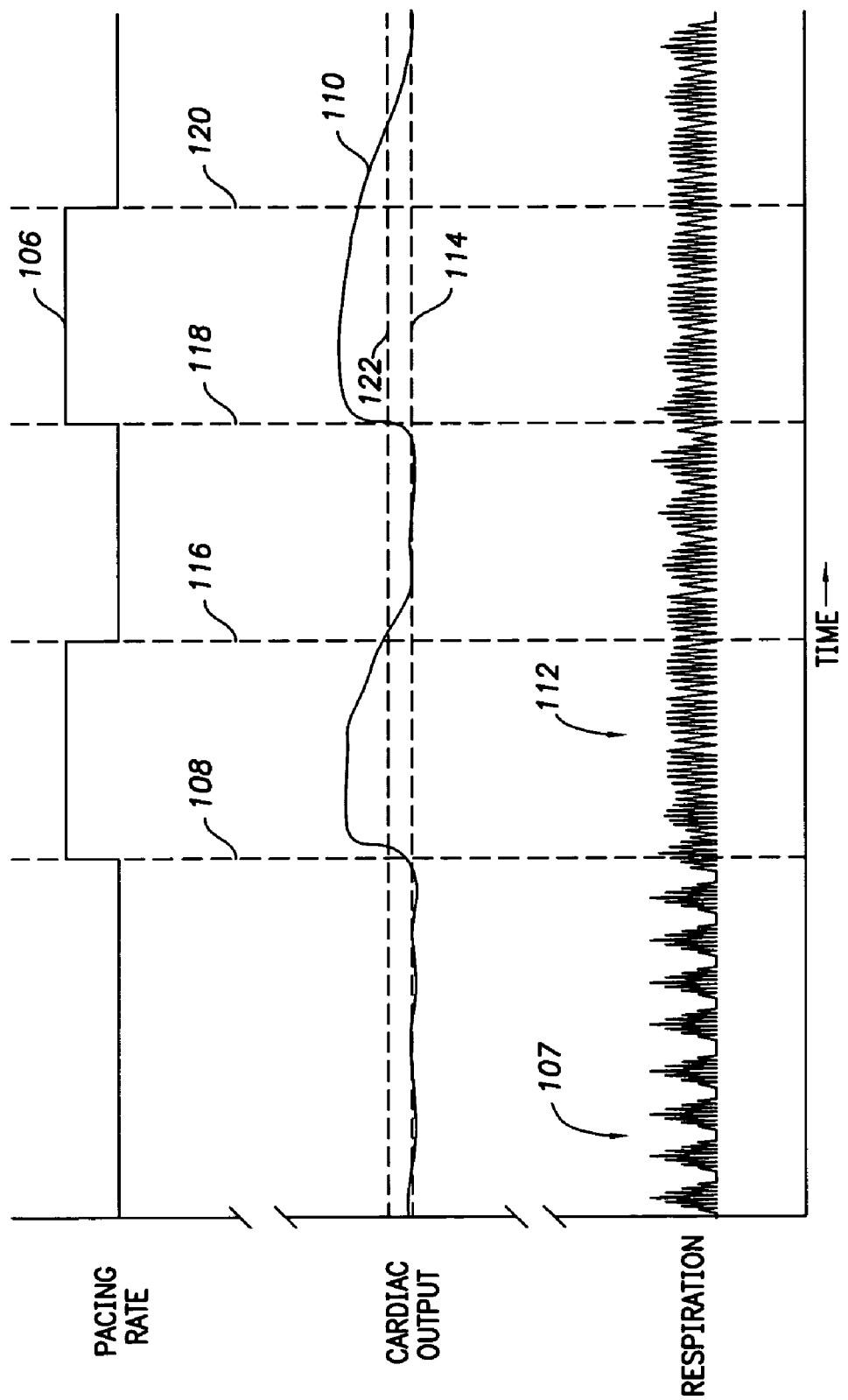
FIG. 4 is a graph illustrating repetitive alteration in pacing rate performed generally in accordance with the technique of FIG. 3 along with resulting cardiac output and respiration curves.
Figure 5:
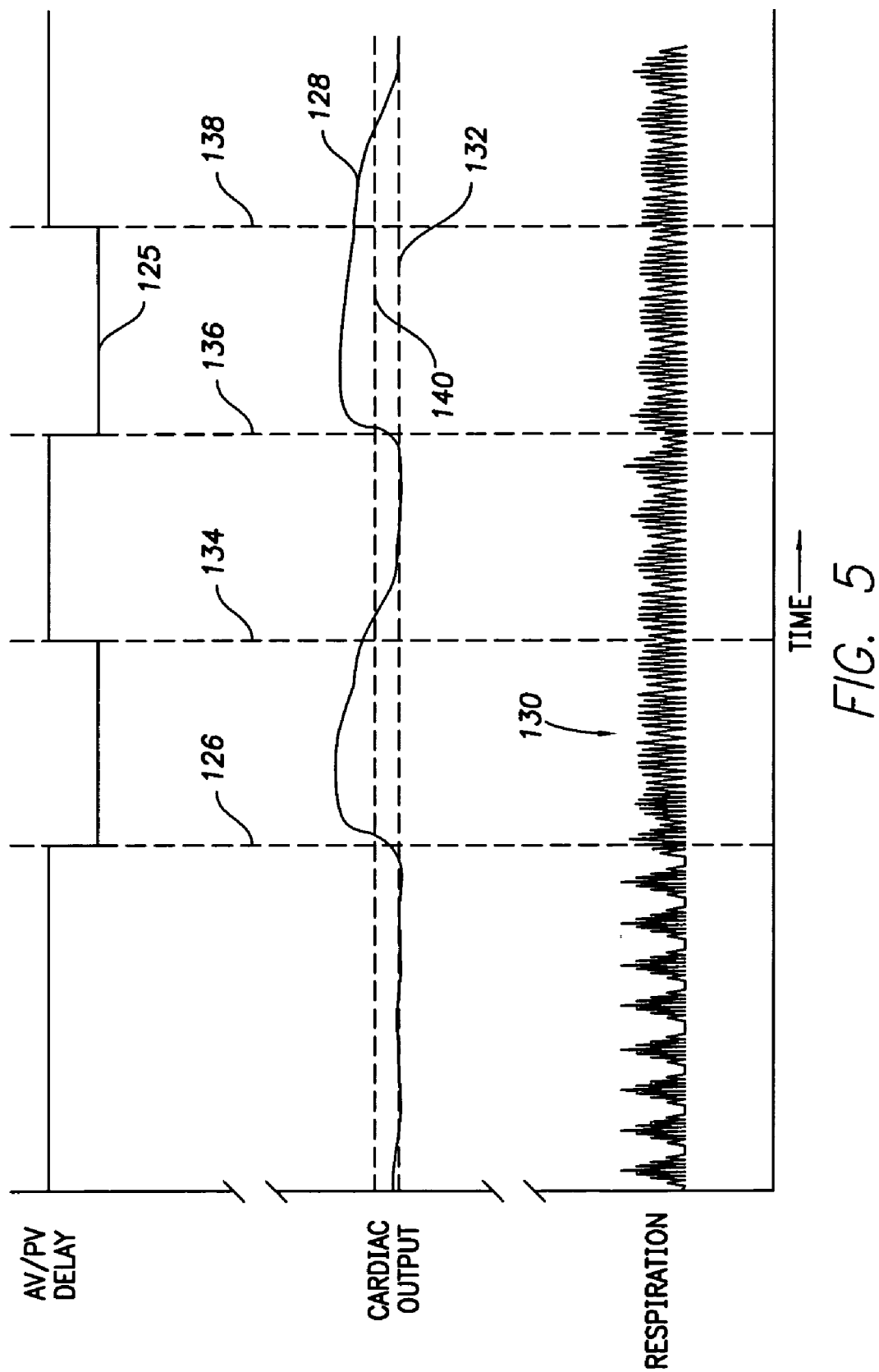
FIG. 5 is a graph illustrating repetitive alteration in AV/PV delay performed generally in accordance with the technique of FIG. 3 along with resulting cardiac output and respiration curves.

Overview of Technique for Elevating Cardiac Output and Suppressing CSR-Induced Apnea/Hypopnea FIGS. 3-5 provide an overview of the techniques of the invention. Initially, at step 100 of FIG. 3, the pacer/ICD temporarily alters a selected pacing parameter—such as the base pacing rate—by an amount sufficient to elevate cardiac output. The elevation in cardiac output is eventually reduced, at least partially, by intrinsic compensatory mechanisms within the patient, such as hemodynamic compensatory mechanisms. At step 102, the pacer/ICD temporarily resets the pacing parameter for a duration sufficient to allow the compensatory mechanisms to return toward its previous state so as to permit a subsequent alteration in the pacing parameter to again elevate cardiac output. At step 104, the pacer/ICD repeatedly alters and resets the pacing parameter so as to achieve an overall increase in cardiac output despite the compensatory mechanisms and to thereby suppress apnea/hypopnea, particularly CSR-induced apnea/hypopnea.

FIG. 4 illustrates an example wherein a ventricular pacing rate 106 is repeatedly altered and reset within a patient suffering from periods of apnea 107 due to CSR. At time 108, the rate is increased from a base pacing rate to an elevated rate, which may be set, e.g., 15 bpm above the base rate. The increase in pacing rate yields a temporary increase in cardiac output 110, which suppresses CSR and allows resumption of more normal respiration 112. The increase in cardiac output is due to the higher pacing rate applied to an initially constant stroke volume. The resumption of more normal respiration is due to mitigation of CSR achieved via the elevated cardiac output. As already explained, intrinsic compensatory mechanisms within the patient, such as hemodynamic mechanisms, soon reduce cardiac output. For example, the intrinsic compensatory mechanisms of a patient might automatically reduce stroke volume to compensate for the artificially increased heart rate. However, before the cardiac output returns to its initial baseline level 114, the pacing rate is reset to the baseline pacing rate, at time 116. This causes the intrinsic compensatory mechanisms to return the hemodynamic state of the patient, at least partially, to its previous state. This permits a subsequent increase in the pacing rate, at time 118, to again elevate cardiac output thus suppressing CSR or at least reducing the severity of CSR. Another reduction in pacing rate is performed at time 120. This cycle is repeated periodically with sequential alterations in pacing rate occurring, e.g., every five minutes. As a result, the average cardiac output 122 achieved is elevated above the initial baseline level 114. Note that CSR may not be completely eliminated and hence the crescendo/decrescendo respiratory pattern may still be present. Indeed, as shown in FIG. 4, the CSR pattern generally remains and starts to become more severe during each interval where cardiac output drops. Nevertheless, in the example of FIG. 4, the severity of CSR is generally diminished to the point where periods of frank apnea no longer arise.

FIG. 5 illustrates an example wherein the AV/PV delay 125 is repeatedly altered, again within a patient suffering from extended periods of reduced respiration due to CSR. At time 126, the AV/PV delay is decreased from a baseline delay value. The reduction in AV/PV delay yields a temporary increase in cardiac output 128, suppression of CSR and resumption of more normal respiration 130. The increase in cardiac output is again due to improved stroke volume. The resumption of more normal respiration is due to mitigation of CSR achieved via the elevated cardiac output. Intrinsic compensatory mechanisms within the patient soon reduce cardiac output. For example, the intrinsic compensatory mechanisms of a patient might automatically reduce the intrinsic heart rate to compensate for the changed AV/PV delay. However, before the cardiac output returns to its initial baseline level 132, the AV/PV delay is reset, at time 134, causing the intrinsic compensatory mechanisms to return the hemodynamic state of the patient, again at least partially, to its previous state. This permits a subsequent reduction in AV/PV delay, at time 136, to again elevate cardiac output, followed by another increase in AV/PV delay at time 138. The cycle is repeated periodically with alterations in AV/PV delay occurring, e.g., every five minutes. As a result, as with the example of FIG. 5, the average cardiac output 140 achieved is elevated above the initial baseline level 132. Note that, as in the example of FIG. 4, CSR may not be completely eliminated and hence the crescendo/decrescendo respiratory pattern may still be present. However, the severity of CSR is again diminished to the point where periods of frank apnea do not arise. In other examples, an increase in AV/PV delay may instead cause the temporary increase in cardiac output. This depends, in part, on the particular patient.

Thus, FIGS. 4 and 5 illustrate two specific examples of pacing parameters that may be selectively altered and reset to achieve an increase in average cardiac output so as to suppress CSR-induced apnea/hypopnea. In some implementations, both parameters may be simultaneously switched. In still other embodiments, the pacing parameter that is altered is the pacing mode, which specifies, at least, the heart chambers to be paced. For example, the device might be programmed to alternate between single-chambered and dual-chambered pacing modes, such as between VVI and DDI. Briefly, the first letter of the three-letter code designates which chamber is paced (A or atrium, V for ventricle, D for both, and O for neither). The second letter designates which chamber is sensed. The third letter designates what action is taken in response to a sense (I for inhibiting delivery of a pacing pulse, T for triggering a pacing pulse, D for both triggering and inhibiting, depending upon the chamber, and O for no action). A fourth letter R is sometimes appended to the code if a rate-adaptive pacing mode is used. Thus, by way of example, DDD indicates a pacing mode wherein the pacer/ICD senses and paces in both the atria and the ventricles and is also capable of both triggering and inhibiting functions based upon events sensed in the atria and the ventricles. VDD indicates a mode wherein the pacer/ICD senses in both the atria and ventricles but only paces in the ventricles. A sensed event on the atrial channel triggers ventricular outputs after a programmable delay. VVI indicates that the pacer/ICD paces and senses only in the ventricles and only capable inhibits the functions based upon events sensed in the ventricles. DDI is identical to DDD except that the pacer/ICD only inhibits functions based upon sensed events, rather than triggering functions. As such, the DDI mode is a non-tracking mode precluding triggering of ventricular outputs in response to sensed atrial events. VOO identifies fixed-rate ventricular pacing, which ignores any potentially sensed cardiac signals. This mode is quite different from the aforementioned "demand" modes, which only pace when the pacemaker determines that the heart is "demanding" pacing. Other pacing modes are possible that are not necessarily represented by three-letter abbreviations of this type. For example, if the pacer/ICD is equipped for biventricular pacing, then the pacing mode may further specify whether pacing or sensing is performed in the LV, the RV or both. Likewise, if the pacer/ICD is equipped for biatrial pacing, then the pacing mode may further specify whether pacing or sensing is performed in the right atrium (RA), the left atrium (LA) or both. As can be appreciated, numerous pacing modes are possible and no attempt is made herein to list all such modes. Routine experimentation may be employed to identify particular combinations of pacing modes that may be exploited using the techniques of the invention to elevate average cardiac output within a patient.

Otherwise routine experimentation may be used to identify still other pacing parameters capable of effecting an increase in average cardiac output. In general, any pacing parameter alteration that yields a temporary increase in cardiac output (that is eventually reduced via intrinsic compensatory mechanisms) is a candidate for use with the techniques of the invention. Also, note that the techniques of the invention may be advantageously exploited to improve cardiac output within patients not prone to CSR-induced apnea/hypopnea. Hence, the techniques of the invention are not limited to suppressing CSR-induced apnea/hypopnea.

Figure 6:
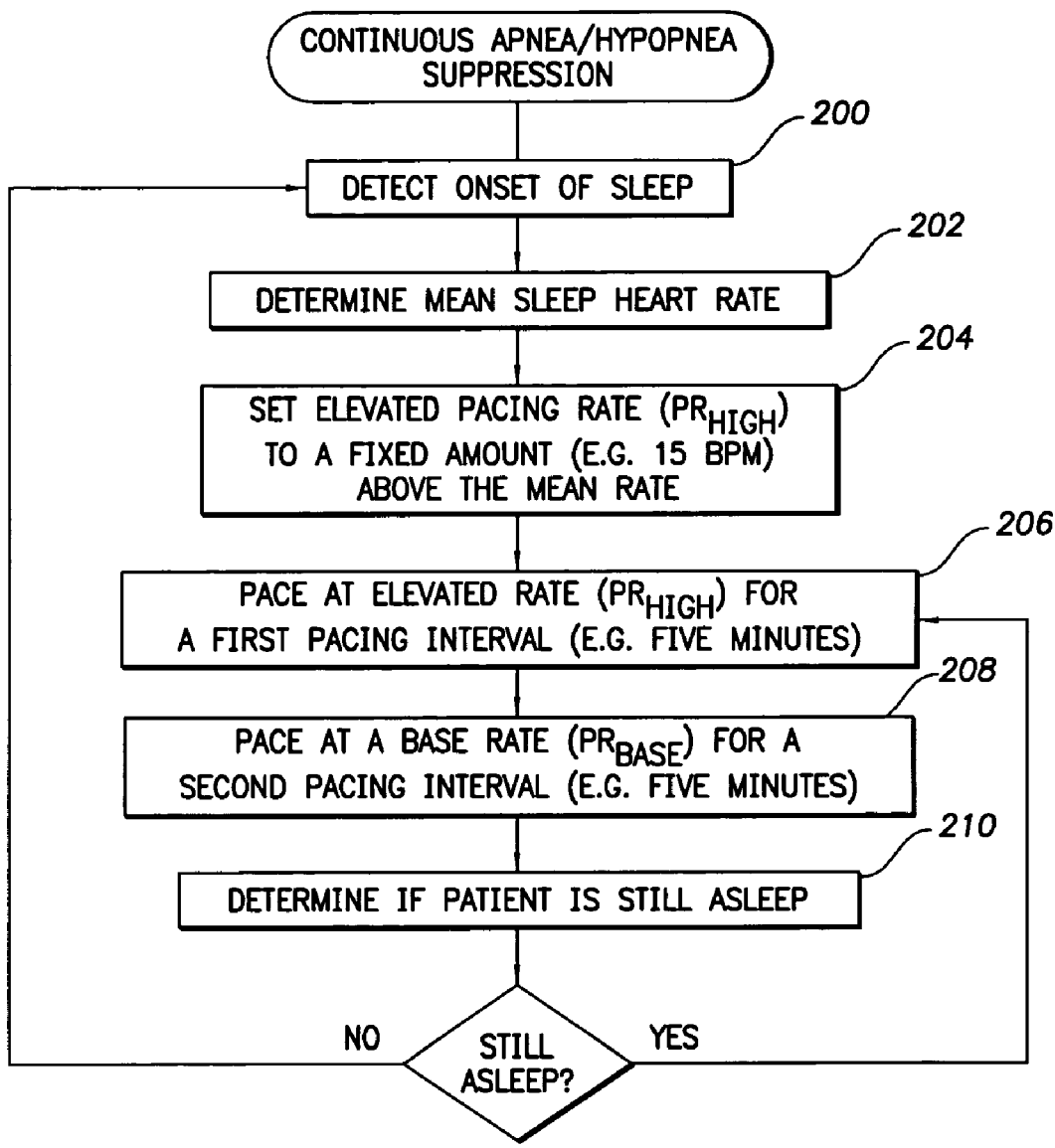
FIG. 6 illustrates a continuous apnea/hypopnea suppression technique performed in accordance with general technique of FIG. 3.
Figure 7:
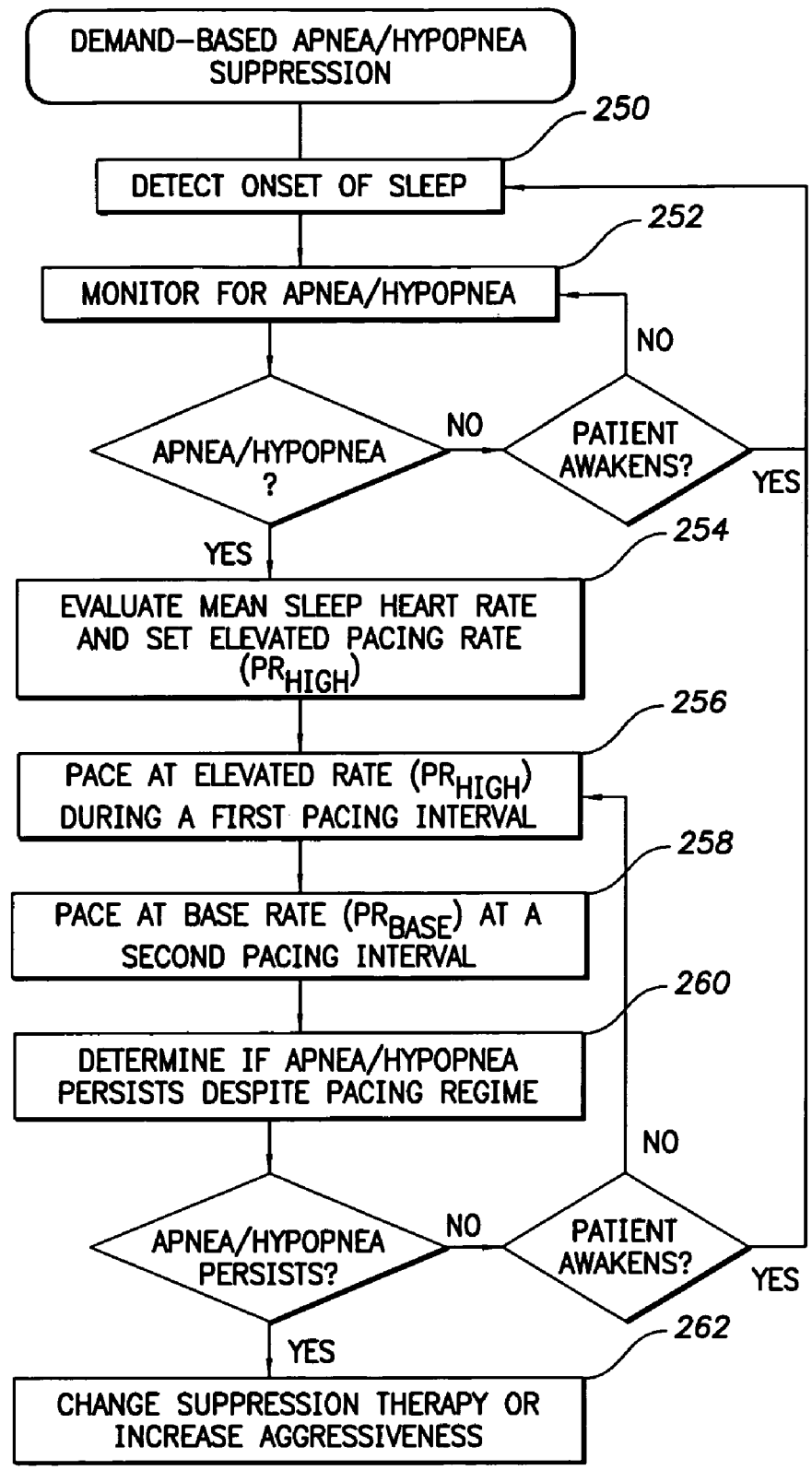
FIG. 7 illustrates a demand-based apnea/hypopnea suppression technique performed in accordance with general technique of FIG. 3.

Turning now to FIGS. 6 and 7, exemplary techniques specifically intended to suppress CSR-induced apnea/hypopnea will be described.

CSR-Induced Apnea/Hypopnea Suppression Examples

FIG. 6 illustrates a continuous CSR-induced apnea/hypopnea suppression technique for use by a pacer/ICD or other implantable medical system, which does not require detection of individual episodes of apnea/hypopnea. Rather, the CSR-induced apnea/hypopnea suppression techniques of FIGS. 3-5 are applied continuously while the patient is asleep to suppress CSR-induced apnea/hypopnea. Typically, the continuous suppression technique of FIG. 6 is only activated within patients known to suffer from episodes CSR. The technique may be selectively activated within the pacer/ICD of the patient by a physician using an external programmer. That is, following device implant, if the physician determines that the patient is prone to episodes of CSR, the physician programs the device to perform the technique of FIG. 6 each night to suppress episodes of CSR-induced apnea/hypopnea.

Beginning at step 200, the pacer/ICD detects the onset of sleep. Any of a variety of predecessor techniques may be used to detect the onset of sleep. Examples are set forth in the following patents or patent applications: U.S. Pat. No. 5,476,483, to Bornzin et al., entitled "System and Method for Modulating the Base Rate During Sleep for a Rate-responsive Cardiac Pacemaker"; U.S. Pat. No. 6,128,534 to Park et al., entitled "Implantable Cardiac Stimulation Device and Method for Varying Pacing Parameters to Mimic Circadian Cycles"; and U.S. patent application Ser. No. 10/339,989, to Koh et al., entitled "System and Method for Detecting Circadian States Using an Implantable Medical Device", filed Jan. 10, 2003. At step 202, the pacer/ICD determines the mean sleep heart rate, i.e. the mean intrinsic heart rate of the patient while asleep. This is also referred to herein as the mean nocturnal heart rate. The mean rate may be determined simply by sensing the intrinsic heart rate after the patient falls asleep. At step 204, the pacer/ICD sets an elevated pacing rate ($PR_{HIGH}$) to a fixed amount (e.g. 15 bpm) above the mean rate.

Figure 8:
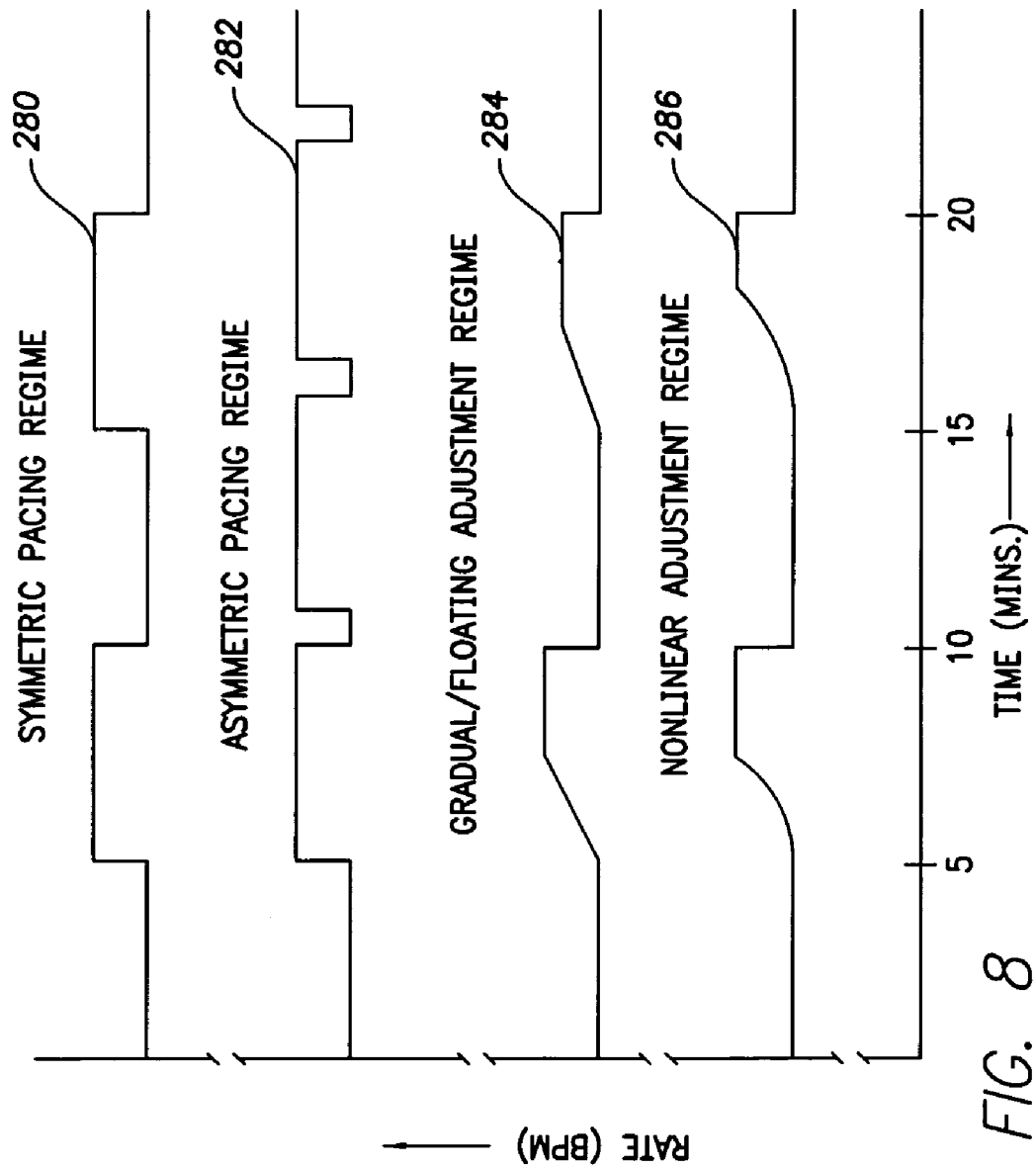
FIG. 8 provides graphs illustrating various exemplary alternating pacing regimes performed in accordance with the general technique of FIG. 3.

At step 206, the pacer/ICD paces the heart of the patient at the elevated rate ($PR_{HIGH}$) for a first pacing interval (e.g. five minutes). At step 208, the pace/ICD paces the heart at a predetermined base rate ($PR_{BASE}$) for a second pacing interval (e.g. another five minutes). The base rate is typically specified by the physician while programming the operation of the pacer/ICD. In some implementations, separate daytime and circadian (or nocturnal) base rates are programmed. The circadian base rate is typically lower than the daytime base rate. In such implementations, the circadian base rate is used at step 208. At step 210, the pacer/ICD determines if the patient is still asleep, again using predecessor techniques. Steps 206-210 are then repeated so long as the patient remains asleep. In this manner, the CSR-induced apnea/hypopnea suppression pacing therapy is delivered throughout the sleep period. Once the patient awakens, processing returns to step 200. Steps 202-210 are then repeated during the next sleep period. One particular advantage of this technique is there is no need for the pacer/ICD to detect individual episodes of apnea/hypopnea. Moreover, the patient benefits from the elevated cardiac output even during nights when there would otherwise have been no apnea/hypopnea. Indeed, the techniques of FIG. 6 can be performed continuously throughout the day to improve cardiac output. However, the repeated alterations in the pacing rate might be unpleasant for some patients if performed while they are awake. Hence, typically, the technique of FIG. 6 is performed only while the patient is known to be asleep. Also, note that the durations of the pacing intervals of steps 206 and 208 need not be equal. In addition, the change from one pacing rate to another need not be immediate and abrupt. Rather, gradual changes may be employed. FIG. 8, discussed below, illustrates some of these alternatives.

FIG. 7 illustrates a demand-based CSR-induced apnea/hypopnea suppression technique, which operates only in response to detection of actual episodes of nocturnal apnea/hypopnea. Many of the steps of FIG. 7 are similar to those of FIG. 6 and only pertinent differences will be described in detail. Beginning at step 250, the pacer/ICD detects the onset of sleep, again using predecessor techniques. At step 252, the pacer/ICD monitors for apnea/hypopnea. Any of a variety of predecessor techniques may be employed, such as the techniques of the patents cited above in the Summary section, particularly techniques described in U.S. patent application Ser. No. 10/883,857, of Koh et al. If no apnea/hypopnea is detected, then step 252 is repeated until the patient eventually awakens. In other words, no suppression therapy is delivered unless and until actual episodes of apnea/hypopnea are detected. If apnea/hypopnea is detected, then steps 254-258 are performed to initiate suppression therapy. These steps generally correspond to steps 202-208 of FIG. 6, and have already been described.

At step 260, the pacer/ICD then determines if apnea/hypopnea persists despite the suppressive pacing regime. If apnea/hypopnea persists, then, at step 262, the particular type of suppression therapy is altered or the existing suppression therapy is made more aggressive. For example, to make the therapy more aggressive, $PR_{HIGH}$ may be increased to, e.g., 25 bpm above $PR_{BASE}$. Although not shown, processing then returns to step 256 for further pacing using the elevated value of $PR_{HIGH}$. In other examples, the device instead changes the suppression technique, i.e. the device selects a different pacing parameter to repetitively alter. For example, the device switches to alternating the AV/PV delay or the pacing mode, instead of the pacing rate. In that case, processing does not return to step 256. Rather, the device engages in an alternate repetitive pacing regime consistent with the new suppression technique. Alternatively, various other apnea/hypopnea responsive therapies may be triggered, if the pacer/ICD is so equipped. See, for example, the techniques described in U.S. patent application Ser. No. 10/844,023, of Koh, cited above. Also, other therapies directed to suppressing CSR may alternatively be triggered. See, e.g., techniques described in U.S. Patent Application 2005/0240240, of Park et al., filed Oct. 27, 2005, entitled "System and Method for Applying Therapy during Hyperpnea Phase of Periodic Breathing using an Implantable Medical Device."

Assuming, however, that apnea/hypopnea does not persist (as determined at step 260), then steps 256-260 are repeated until the patient awakens naturally. Thus, with the technique of FIG. 7, once CSR-induced apnea/hypopnea suppression therapy is activated upon detection of a first episode of apnea/hypopnea during a given sleep interval, the suppression therapy continues until the patient awakens, even if no further episodes of apnea/hypopnea are specifically detected.

Turning now to FIG. 8, various exemplary alternating pacing regimes are illustrated. A first exemplary regime 282 is symmetric, i.e. the higher and lower pacing rates are applied for equal intervals of time. In this particular example, the intervals are five minutes each. A second exemplary regime 284 is asymmetric, i.e. the higher and lower pacing rates are applied for unequal intervals of time. In this particular example, the higher rate intervals are five minutes each, whereas the lower rate intervals are only one minute each. A third exemplary regime 286 exhibits a gradual, linear increase in pacing rate from the lower rate to the higher rate, followed by an abrupt decrease back down to the lower rate. Alternatively, the increase from the lower rate to the upper rate may be immediate, whereas the decrease from the upper rate to the lower rate might be gradual. In still other examples, both transitions are gradual. Regime 286 also illustrates that the target rates may "float" that is the device need not cycle between fixed rates. In the specific example of regime 286, the second upper rate level is somewhat lower than the first upper rate level. A fourth exemplary regime 288, illustrates a non-linear, gradual regime, alternating between fixed upper and lower rates. The rate increases are both non-linear, i.e. the rate increases slowly at first then increases more quickly. Moreover, regime 288 illustrates the time interval during which the rate increases may vary from cycle to cycle. In the specific example of regime 288, the second non-linear rate increase is performed over a longer period of time. In yet other implementations, rather than using just upper and lower pacing rates, the pacer/ICD may cycle through various intermediate rates, e.g. a middle pacing rate may be defined in addition to the upper and lower rates. As already noted, multiple parameters may be changed at once (or in succession), such as changes to both pacing rate and AV/PV delay. For example, the device might first alternate pacing rate for one cycle then alternate AV/PV delay for the next cycle, before yet again alternating the pacing rate, and so on. As can be appreciated a wide variety of different alternating pacing regimes may be provided in accordance with the general principles of the invention and no attempt is made here to describe all possible variations. Otherwise routine experimentation may be used to identify optimal pacing regimes or combinations of regimes that optimize cardiac output.

Preferably, the duration of the intervals, the relative difference between the various pacing rates, and the rate of change from one rate to another are all optimized to maximize cardiac output. In this regard, otherwise routine experimentation may be performed to optimize these parameters. In one example, the physician conducts various tests with a given patient to determine the optimal values for use with that particular patient. This may be achieved, for example, by pacing the heart of the patient with the parameters set to various values while monitoring cardiac output to determine which parameters are most effective. If the device itself is equipped to evaluate cardiac output, such optimization techniques may be performed periodically by the device itself to automatically reset the various parameters. Techniques for detecting cardiac output within a patient using an implantable medical device are described, e.g., in U.S. patent application Ser. No. 11/267,665, filed Nov. 4, 2005, of Kil et al., entitled "System and Method for Measuring Cardiac Output via Thermal Dilution using an Implantable Medical Device with Thermistor Implanted in Right Ventricle".

Exemplary Pacemaker/ICD

Figure 1:
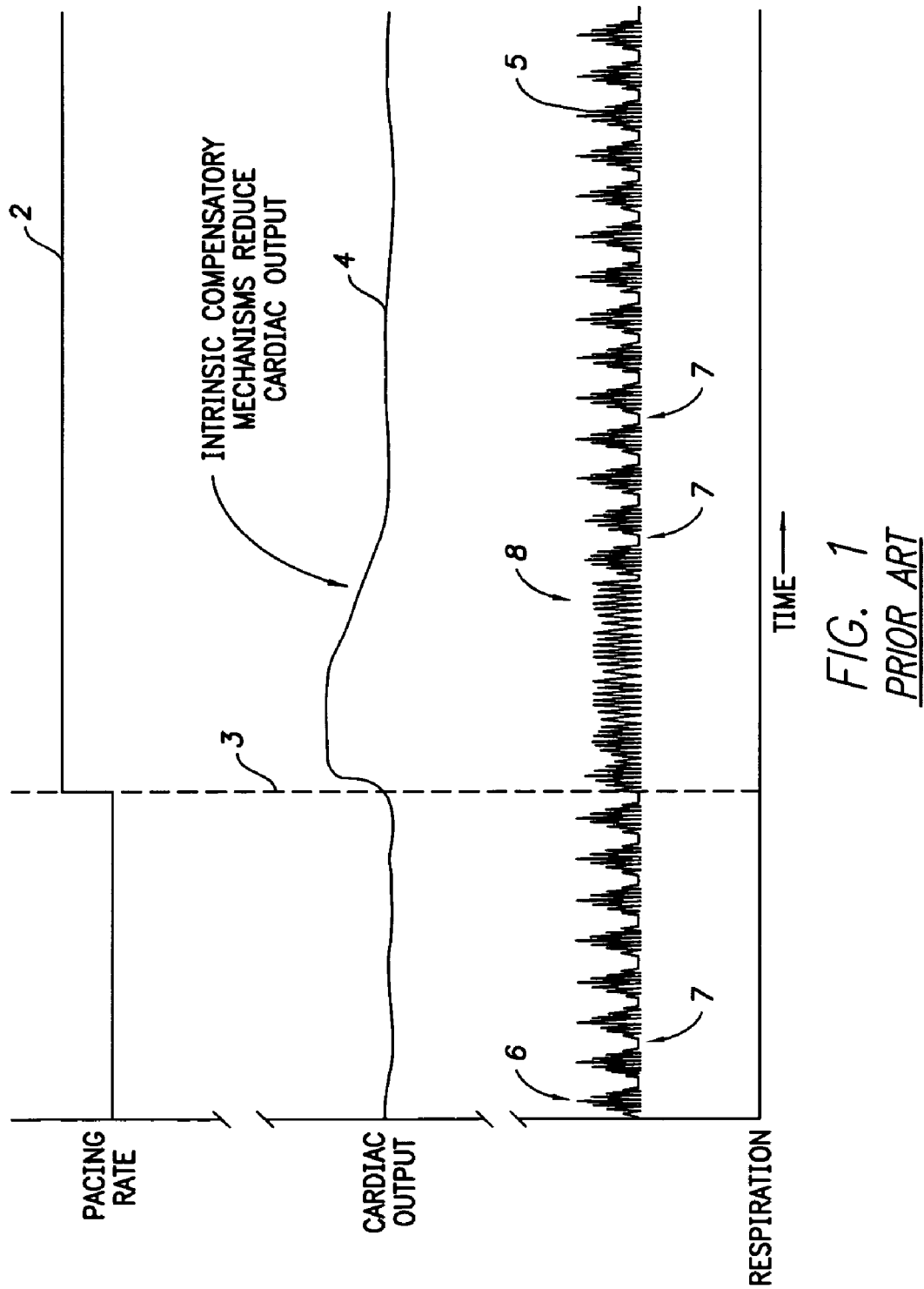
FIG. 1 is a graph illustrating the effect of intrinsic compensatory mechanisms on cardiac output and respiration following a sustained increase in pacing rate in accordance with prior art techniques.
Figure 10:
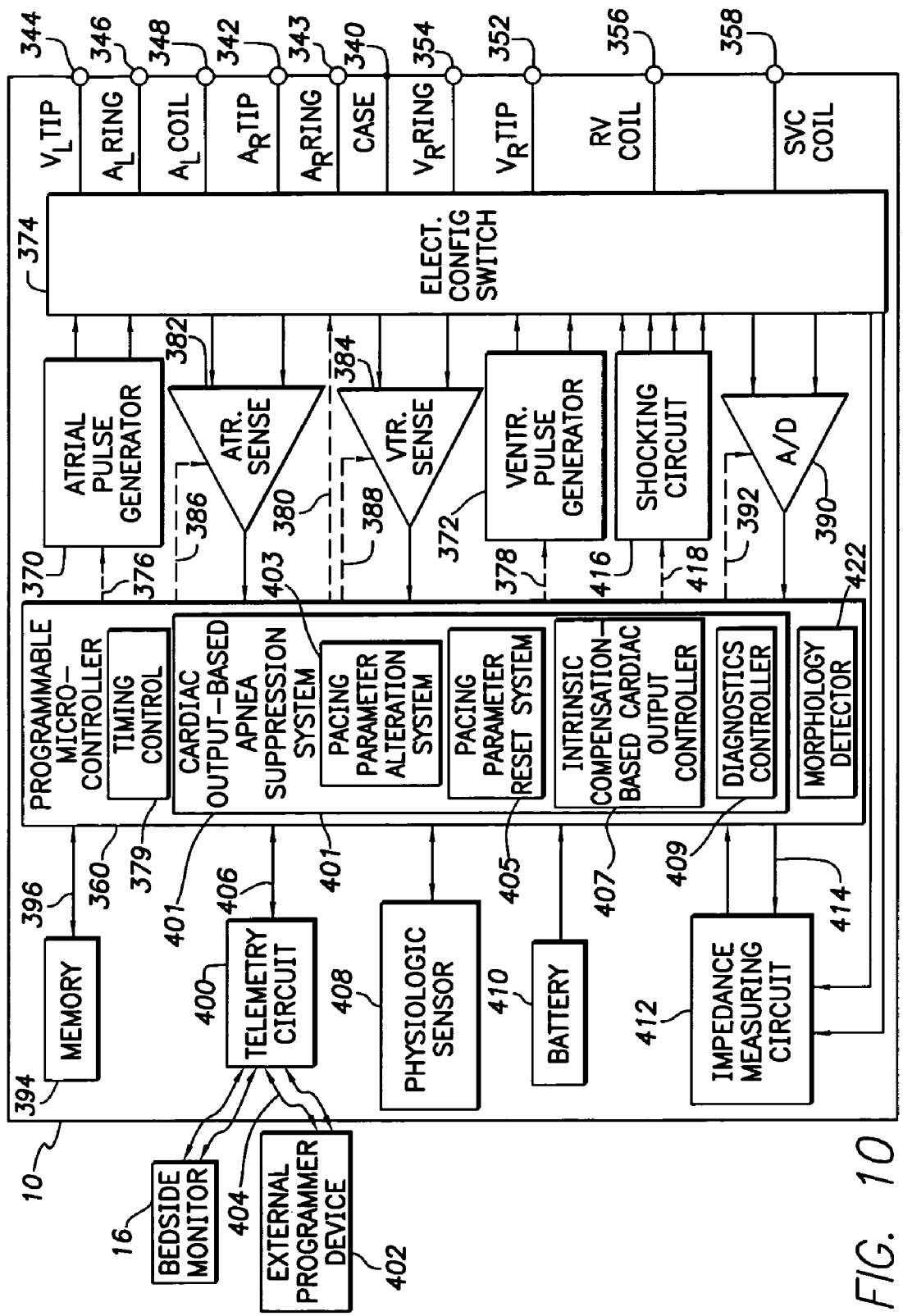
FIG. 10 is a functional block diagram of the pacer/ICD of FIG. 9, illustrating basic circuit elements that provide cardioversion, defibrillation and/or pacing stimulation in four chambers of the heart and particularly illustrating components of the cardiac output-based apnea/hypopnea suppression system.

With reference to FIGS. 9 and 10, a detailed description of the pacer/ICD of FIG. 1 will now be provided. More specifically, FIG. 9 provides a block diagram of an exemplary dual-chamber stimulation device capable of treating both fast and slow arrhythmias with stimulation therapy, including cardioversion, defibrillation, and pacing stimulation, as well as capable of elevating cardiac output and suppressing CSR-induced apnea/hypopnea.

To provide atrial chamber pacing stimulation and sensing, pacer/ICD 10 is shown in electrical communication with a heart 312 by way of a right atrial lead 320 having an atrial tip electrode 322 and an atrial ring electrode 323 implanted in the atrial appendage. Pacer/ICD 10 is also in electrical communication with the heart by way of a right ventricular lead 330 having, in this embodiment, a ventricular tip electrode 332, a right ventricular ring electrode 334, a right ventricular (RV) coil electrode 336, and a superior vena cava (SVC) coil electrode 338. Typically, the right ventricular lead 330 is transvenously inserted into the heart so as to place the RV coil electrode 336 in the right ventricular apex, and the SVC coil electrode 338 in the superior vena cava. Accordingly, the right ventricular lead is capable of receiving cardiac signals, and delivering stimulation in the form of pacing and shock therapy to the right ventricle.

To sense left atrial and ventricular cardiac signals and to provide left chamber pacing therapy, pacer/ICD 10 is coupled to a "coronary sinus" lead 324 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 324 is designed to receive atrial and ventricular cardiac signals and to deliver left ventricular pacing therapy using at least a left ventricular tip electrode 326, left atrial pacing therapy using at least a left atrial ring electrode 327, and shocking therapy using at least a left atrial coil electrode 328. With this configuration, biventricular pacing can be performed. Although only three leads are shown in FIG. 9, it should also be understood that additional stimulation leads (with one or more pacing, sensing and/or shocking electrodes) may be used in order to efficiently and effectively provide pacing stimulation to the left side of the heart or atrial cardioversion and/or defibrillation.

A simplified block diagram of internal components of pacer/ICD 10 is shown in FIG. 10. While a particular pacer/ICD is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation as well as providing for the aforementioned therapy.

The housing 340 for pacer/ICD 10, shown schematically in FIG. 10, is often referred to as the "can", "case" or "case electrode" and may be programmably selected to act as the return electrode for all "unipolar" modes. The housing 340 may further be used as a return electrode alone or in combination with one or more of the coil electrodes, 328, 336 and 338, for shocking purposes. The housing 340 further includes a connector (not shown) having a plurality of terminals, 342, 343, 344, 346, 348, 352, 354, 356 and 358 (shown schematically and, for convenience, the names of the electrodes to which they are connected are shown next to the terminals). As such, to achieve right atrial sensing and pacing, the connector includes at least a right atrial tip terminal ($A_R$ TIP) 342 adapted for connection to the atrial tip electrode 322 and a right atrial ring ($A_R$ RING) electrode 343 adapted for connection to right atrial ring electrode 323. To achieve left chamber sensing, pacing and shocking, the connector includes at least a left ventricular tip terminal ($V_L$ TIP) 344, a left atrial ring terminal ($A_L$ RING) 346, and a left atrial shocking terminal ($A_L$ COIL) 348, which are adapted for connection to the left ventricular ring electrode 326, the left atrial tip electrode 327, and the left atrial coil electrode 328, respectively. To support right chamber sensing, pacing and shocking, the connector further includes a right ventricular tip terminal ($V_R$ TIP) 352, a right ventricular ring terminal ($V_R$ RING) 354, a right ventricular shocking terminal ($R_V$ COIL) 356, and an SVC shocking terminal (SVC COIL) 358, which are adapted for connection to the right ventricular tip electrode 332, right ventricular ring electrode 334, the RV coil electrode 336, and the SVC coil electrode 338, respectively.

At the core of pacer/ICD 10 is a programmable microcontroller 360, which controls the various modes of stimulation therapy. As is well known in the art, the microcontroller 360 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 360 includes the ability to process or monitor input signals (data) as controlled by a program code stored in a designated block of memory. The details of the design and operation of the microcontroller 360 are not critical to the invention. Rather, any suitable microcontroller 360 may be used that carries out the functions described herein. The use of microprocessor-based control circuits for performing timing and data analysis functions are well known in the art.

As shown in FIG. 10, an atrial pulse generator 370 and a ventricular pulse generator 372 generate pacing stimulation pulses for delivery by the right atrial lead 320, the right ventricular lead 330, and/or the coronary sinus lead 324 via an electrode configuration switch 374. It is understood that in order to provide stimulation therapy in each of the four chambers of the heart, the atrial and ventricular pulse generators, 370 and 372, may include dedicated, independent pulse generators, multiplexed pulse generators or shared pulse generators. The pulse generators, 370 and 372, are controlled by the microcontroller 260 via appropriate control signals, 276 and 278, respectively, to trigger or inhibit the stimulation pulses.

The microcontroller 360 further includes timing control circuitry (not separately shown) used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 374 includes a plurality of switches for connecting the desired electrodes to the appropriate I/O circuits, thereby providing complete electrode programmability. Accordingly, the switch 374, in response to a control signal 380 from the microcontroller 360, determines the polarity of the stimulation pulses (e.g., unipolar, bipolar, combipolar, etc.) by selectively closing the appropriate combination of switches (not shown) as is known in the art.

Atrial sensing circuits 382 and ventricular sensing circuits 384 may also be selectively coupled to the right atrial lead 320, coronary sinus lead 324, and the right ventricular lead 330, through the switch 374 for detecting the presence of cardiac activity in each of the four chambers of the heart. Accordingly, the atrial (ATR. SENSE) and ventricular (VTR. SENSE) sensing circuits, 382 and 384, may include dedicated sense amplifiers, multiplexed amplifiers or shared amplifiers. The switch 374 determines the "sensing polarity" of the cardiac signal by selectively closing the appropriate switches, as is also known in the art. In this way, the clinician may program the sensing polarity independent of the stimulation polarity. Each sensing circuit, 382 and 384, preferably employs one or more low power, precision amplifiers with programmable gain and/or automatic gain control and/or automatic sensitivity control, bandpass filtering, and a threshold detection circuit, as known in the art, to selectively sense the cardiac signal of interest. The automatic gain control enables pacer/ICD 10 to deal effectively with the difficult problem of sensing the low amplitude signal characteristics of atrial or ventricular fibrillation. The outputs of the atrial and ventricular sensing circuits, 382 and 384, are connected to the microcontroller 360 which, in turn, are able to trigger or inhibit the atrial and ventricular pulse generators, 370 and 372, respectively, in a demand fashion in response to the absence or presence of cardiac activity in the appropriate chambers of the heart.

For arrhythmia detection, pacer/ICD 10 utilizes the atrial and ventricular sensing circuits, 382 and 384, to sense cardiac signals to determine whether a rhythm is physiologic or pathologic. As used in this section "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 360 by comparing them to a predefined rate zone limit (i.e., bradycardia, normal, atrial tachycardia, atrial fibrillation, low rate ventricular tachycardia (VT), high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 390. The data acquisition system 390 is configured to acquire intracardiac electrogram signals, convert the raw analog data into a digital signal, and store the digital signals for later processing and/or telemetric transmission to an external device 402. The data acquisition system 390 is coupled to the right atrial lead 320, the coronary sinus lead 324, and the right ventricular lead 330 through the switch 374 to sample cardiac signals across any pair of desired electrodes. The microcontroller 360 is further coupled to a memory 394 by a suitable data/address bus 396, wherein the programmable operating parameters used by the microcontroller 360 are stored and modified, as required, in order to customize the operation of pacer/ICD 10 to suit the needs of a particular patient. Such operating parameters define, for example, pacing pulse amplitude or magnitude, pulse duration, electrode polarity, rate, sensitivity, automatic features, arrhythmia detection criteria, and the amplitude, waveshape and vector of each shocking pulse to be delivered to the patient's heart within each respective tier of therapy. Other pacing parameters include base rate, rest rate and circadian base rate and the aforementioned parameters relevant to the cardiac output enhancement and CSR-induced apnea/hypopnea suppression techniques of the invention.

Advantageously, the operating parameters of the implantable pacer/ICD 10 may be non-invasively programmed into the memory 394 through a telemetry circuit 400 in telemetric communication with the external device 402, such as a programmer, transtelephonic transceiver or a diagnostic system analyzer. The telemetry circuit 400 is activated by the microcontroller by a control signal 406. The telemetry circuit 400 advantageously allows intracardiac electrograms and status information relating to the operation of pacer/ICD 10 (as contained in the microcontroller 360 or memory 394) to be sent to the external device 402 through an established communication link 404. In the preferred embodiment, pacer/ICD 10 further includes a physiologic sensor 408, commonly referred to as a "rate-responsive" sensor because it is typically used to adjust pacing stimulation rate according to the exercise state of the patient. However, the physiological sensor 408 may further be used to detect changes in cardiac output, changes in the physiological condition of the heart, or diurnal changes in activity (e.g., detecting sleep and wake states). Accordingly, the microcontroller 360 responds by adjusting the various pacing parameters (such as rate, AV Delay, V-V Delay, etc.) at which the atrial and ventricular pulse generators, 370 and 372, generate stimulation pulses. While shown as being included within pacer/ICD 10, it is to be understood that the physiologic sensor 408 may also be external to pacer/

ICD 10, yet still be implanted within or carried by the patient. A common type of rate responsive sensor is an activity sensor, such as an accelerometer or a piezoelectric crystal, which is mounted within the housing 340 of pacer/ICD 10. Other types of physiologic sensors are also known, for example, sensors that sense the oxygen content of blood, respiration rate and/or minute ventilation, pH of blood, ventricular gradient, etc.

The pacer/ICD additionally includes a battery 410, which provides operating power to all of the circuits shown in FIG. 10. The battery 410 may vary depending on the capabilities of pacer/ICD 10. If the system only provides low voltage therapy, a lithium iodine or lithium copper fluoride cell may be utilized. For pacer/ICD 10, which employs shocking therapy, the battery 410 must be capable of operating at low current drains for long periods, and then be capable of providing high-current pulses (for capacitor charging) when the patient requires a shock pulse. The battery 410 must also have a predictable discharge characteristic so that elective replacement time can be detected. Accordingly, pacer/ICD 10 is preferably capable of high voltage therapy and employs lithium/silver vanadium oxide batteries, as is true for most (if not all) current devices. As further shown in FIG. 10, pacer/ICD 10 is shown as having an impedance measuring circuit 412 which is enabled by the microcontroller 360 via a control signal 414. Here, thoracic impedance is primarily detected for use in tracking thoracic respiratory oscillations. Other uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 120 is advantageously coupled to the switch 74 so that any desired electrode may be used.

In the case where pacer/ICD 10 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 360 further controls a shocking circuit 416 by way of a control signal 418. The shocking circuit 416 generates shocking pulses of low (up to 0.5 joules), moderate (0.5-10 joules) or high energy (11 to 40 joules), as controlled by the microcontroller 360. Such shocking pulses are applied to the heart of the patient through at least two shocking electrodes, and as shown in this embodiment, selected from the left atrial coil electrode 328, the RV coil electrode 336, and/or the SVC coil electrode 338. The housing 340 may act as an active electrode in combination with the RV electrode 336, or as part of a split electrical vector using the SVC coil electrode 338 or the left atrial coil electrode 328 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 360 is capable of controlling the synchronous or asynchronous delivery of the shocking pulses.

Microcontroller 360 also includes components directed to increasing cardiac output and suppressing CSR-induced apnea/hypopnea. In particular, a cardiac output-based apnea suppression system 401 is operative to control the enhancement of cardiac output and the suppression of CSR-induced apnea/hypopnea using the techniques general described above with reference to FIGS. 1-8. System 401 includes a pacing parameter alteration system 403 operative to temporarily alter a selected pacing parameter by an amount sufficient to elevate cardiac output, the elevation in cardiac output being eventually reduced by intrinsic compensatory mechanisms within the patient. System 401 also includes a pacing parameter reset system 405 operative to temporarily reset the selected pacing parameter for a duration sufficient to allow the compensatory mechanisms to return toward a previous state so as to permit a subsequent alteration in the pacing parameter to again elevate cardiac output. Additionally, system 401 includes an intrinsic compensation-based cardiac output controller 407 operative to control the alteration system and the reset system to repeatedly alter and reset the pacing parameter so as to achieve an overall increase in cardiac output despite the intrinsic compensatory mechanisms. System 401 optionally includes a diagnostic controller 409 for controlling the generation of diagnostic data pertinent to the invention, such as the trending of CSR severity and information indicative of the effectiveness of the CSR-induced apnea/hypopnea suppression techniques. Depending upon the particular implementation, the various components of the microcontroller may be implemented as separate software modules or the modules may be combined to permit a single module to perform multiple functions. In addition, although shown as being components of the microcontroller, some or all of these components may be implemented separately from the microcontroller.

In general, while the invention has been described with reference to particular embodiments, modifications can be made thereto without departing from the scope of the invention. Note also that the term "including" as used herein is intended to be inclusive, i.e. "including but not limited to."

What is claimed is:

1. A method for improving cardiac output within a patient using an implantable medical device equipped to deliver cardiac pacing in accordance with one or more adjustable pacing parameters, the method comprising:

altering a selected pacing parameter to increase cardiac output and then delivering cardiac pacing using the altered parameter for a duration sufficient to elevate cardiac output within the patient relative to a pre-alteration cardiac output level, the elevation in cardiac output being eventually reduced by intrinsic compensatory mechanisms within the patient despite sustained cardiac pacing using the altered parameter;

resetting the pacing parameter for a duration sufficient to allow the compensatory mechanisms to return toward a previous state so as to permit a subsequent alteration in the pacing parameter to again elevate cardiac output; and repeatedly altering and resetting the pacing parameter so as to achieve an overall increase in cardiac output despite the intrinsic compensatory mechanisms of the patient.

2. The method of claim 1 wherein the pacing parameter that is repeatedly altered and reset is a ventricular pacing rate.

3. The method of claim 2 wherein the step of altering the pacing parameter to increase cardiac output is performed by temporarily increasing the ventricular pacing rate by an amount sufficient to achieve a significant increase in cardiac output relative to the pre-alteration cardiac output level; and wherein the step of resetting the pacing parameter is performed by temporarily decreasing the ventricular pacing rate so as to permit a subsequent increase in pacing rate to again elevate cardiac output.

4. The method of claim 3 wherein repeatedly altering and resetting the ventricular pacing rate is performed over time intervals each of at least one minute in length.

5. The method of claim 3 wherein repeatedly altering and resetting the ventricular pacing rate is performed by abruptly change pacing rates.

6. The method of claim 3 wherein repeatedly altering and resetting the ventricular pacing rate is performed by gradually change ventricular pacing rates.

7. The method of claim 6 wherein the gradual changes to the ventricular pacing rate are non-linear.

8. The method of claim 3 wherein repeatedly altering and resetting the pacing parameter is performed over time intervals sufficient to maximize cardiac output.

9. The method of claim 1 wherein the pacing parameter that is repeatedly altered and reset is an AV/PV delay value.

10. The method of claim 1 wherein repeatedly altering and resetting the pacing parameter is performed over intervals of time selected to minimize episodes of reduced respiration within the patient.

11. The method of claim 10 further comprising detecting an episode of reduced respiration and wherein repeatedly altering and resetting the pacing parameter is performed only during episodes of reduced respiration.

12. The method of claim 11 wherein detecting an episode of reduced respiration is performed to detect apnea/hypopnea associated with Cheyne-Stokes Respiration (CSR).

13. A system for use in an implantable medical device for implant within a patient, the device equipped to deliver cardiac pacing in accordance with one or more adjustable pacing parameters, the system comprising:

a pacing parameter alteration system operative to alter a selected pacing parameter to increase cardiac output and further operative to deliver cardiac pacing using the altered parameter for a duration sufficient to elevate cardiac output within the patient relative to a pre-alteration cardiac output level, the elevation in cardiac output being eventually reduced by intrinsic compensatory mechanisms within the patient despite sustained cardiac pacing using the altered parameter;

a pacing parameter reset system operative to reset the selected pacing parameter for a duration sufficient to allow the compensatory mechanisms to return toward a previous state so as to permit a subsequent alteration in the pacing parameter to again elevate cardiac output; and an intrinsic compensation-based cardiac output controller operative to control the alteration system and the reset system to repeatedly alter and reset the pacing parameter so as to achieve an overall increase in cardiac output despite the intrinsic compensatory mechanisms of the patient.

14. The system of claim 13 wherein the pacing parameter alteration system is operative to alter a ventricular pacing rate.

15. The system of claim 13 wherein the system components are operative to alter and reset the pacing parameter over time intervals sufficient to maximize cardiac output.

16. A system for use in an implantable medical device for implant within a patient, the system comprising:

means for altering a selected pacing parameter to increase cardiac output and for delivering cardiac pacing using the altered parameter for a duration sufficient to elevate cardiac output within the patient relative to a pre-alteration cardiac output level, the elevation in cardiac output being eventually reduced by intrinsic compensatory mechanisms within the patient despite sustained cardiac pacing using the altered parameter;

means for resetting the selected pacing parameter for a duration sufficient to allow the compensatory mechanisms to return toward a previous state so as to permit a subsequent alteration in the pacing parameter to again elevate cardiac output; and means for repeatedly altering and resetting the pacing parameter so as to achieve an overall increase in cardiac output despite the intrinsic compensatory mechanisms of the patient.

17. The system of claim 16 wherein the means for altering a selected pacing parameter comprises means for increasing a ventricular pacing rate.

18. The system of claim 17 wherein the means for repeatedly altering and resetting the ventricular pacing rate operates over time intervals of at least one minute in length.

19. The system of claim 16 wherein the means for repeatedly altering and resetting the pacing parameter comprises means for altering and resetting the pacing parameter over time intervals sufficient to maximize cardiac output.

20. The system of claim 16 wherein the means for repeatedly altering and resetting the pacing parameter comprises means for altering and resetting the pacing parameter over time intervals sufficient to minimize episodes of reduced respiration within the patient.

* * * * *